US00PP18657P3

(12) United States Plant Patent
Meillland

(10) Patent No.: US PP18,657 P3
(45) Date of Patent: Mar. 25, 2008

(54) FLORIBUNDA ROSE PLANT NAMED 'MEIPOJONA'

(50) Latin Name: *Rosa hybrida*
Varietal Denomination: Meipojona

(75) Inventor: Alain A. Meillland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 12 days.

(21) Appl. No.: 11/476,067

(22) Filed: Jun. 28, 2006

(65) Prior Publication Data

US 2007/0192912 P1 Aug. 16, 2007

(30) Foreign Application Priority Data

Feb. 13, 2006 (EP) ..... 2006/0439

(51) Int. Cl.
*A01H 5/00* (2006.01)

(52) U.S. Cl. ..... Plt./145

(58) Field of Classification Search ..... Plt./145
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct Floribunda rose plant is provided that originated as a branch sport of the 'Meipomolo' variety (U.S. Plant Pat. No. 16,342). Unlike the 'Meipomolo' variety, the new variety forms golden-yellow blossoms instead of yellow-orange blossoms. The attractive blossoms are formed on a nearly continuous basis. The growth habit is vigorous and bushy. The semi-glossy foliage is dense dark green and of good substance and contrasts nicely with the golden-yellow blossom coloration. Very good tolerance to Black Spot and Oidium is displayed under normal growing conditions. The plant is well suited for growing as attractive ornamentation in parks and gardens.

2 Drawing Sheets

Figure 1:
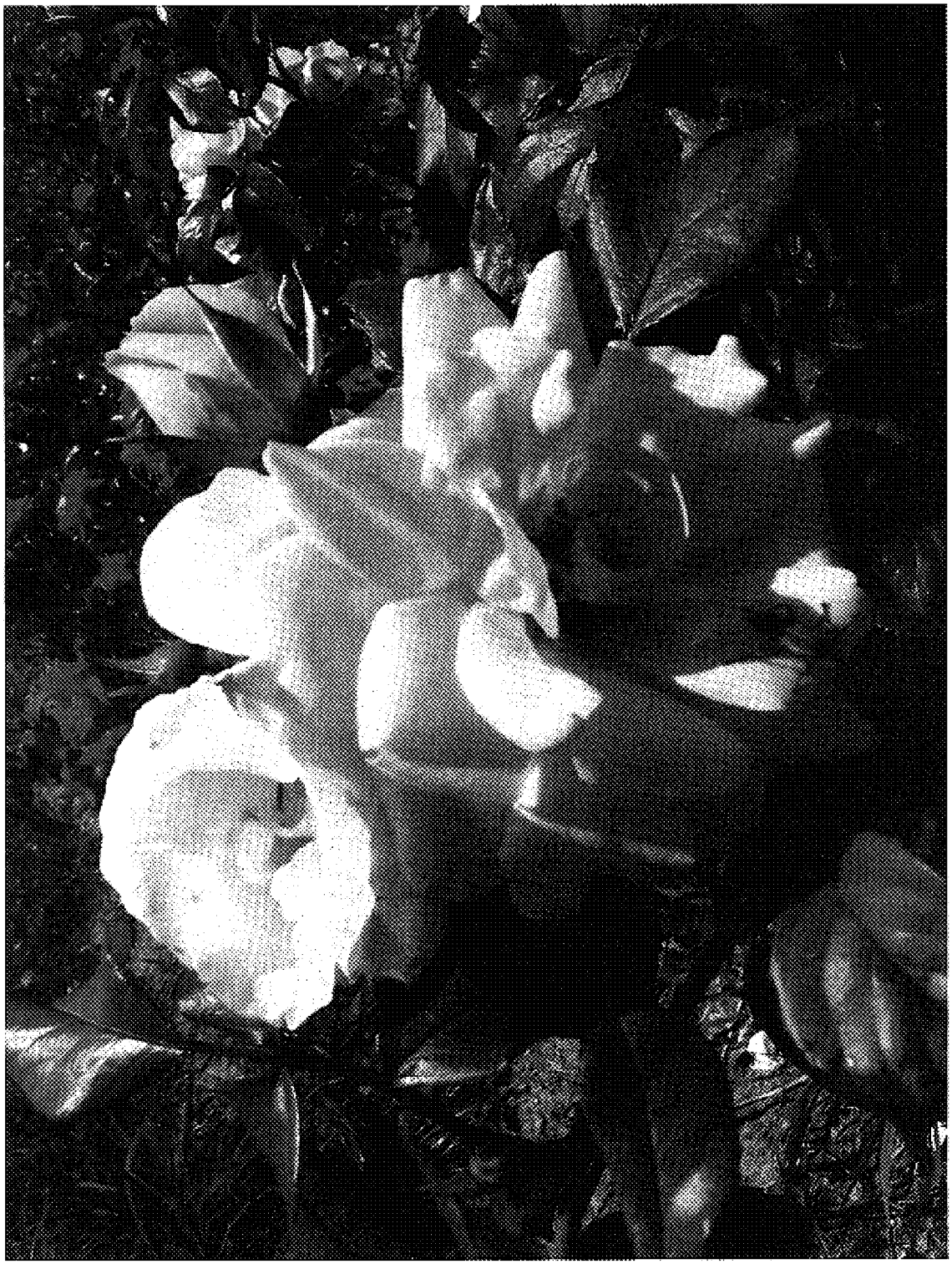

Botanical/commercial classification: *Rosa hybrida*/Floribunda Rose Plant.
Varietal denomination: cv. 'Meipojona'.

SUMMARY OF THE INVENTION

A single plant of the new variety was discovered as a branch sport at Le Cannet - Des - Maures, Le Luc, France, while growing in rose fields among plants of the 'Meipomolo' variety (U.S. Plant Pat. No. 16,342). The mutation was of unknown causation. I was attracted to the plant primarily because of its distinctive flower coloration. Subsequently the plant has undergone detailed observation and study. Had I not discovered and preserved the new plant it would have been lost to mankind.

It was found that the new variety of Floribunda rose plant of the present invention possesses the following combination of characteristics:

(a) forms on a nearly continuous basis attractive bright golden-yellow blossoms, (b) exhibits a vigorous and bushy growth habit, (c) forms decorative dense dark green semi-glossy foliage of good substance, (d) displays good tolerance to Oidium and Black Spot, and (e) is well suited for growing as attractive ornamentation in parks and gardens.

The golden-yellow blossom coloration is luminous in character and contrasts nicely with the dark green foliage. The plant is well suited for growing in U.S.D.A. Hardiness Zone No. 6.

The new variety of the present invention can be readily distinguished from its 'Meipomolo' ancestor. More specifically, the blossoms of the 'Meipomolo' variety are yellow-orange unlike the golden-yellow coloration of the new variety.

The new variety of the present invention also can be readily distinguished from other similar Floribunda rose varieties, such as the 'Meibeausai' (U.S. Plant Pat. No. 7,667) and 'Meimonblan' (U.S. Plant Pat. No. 12,579) varieties. Each forms blossoms having a different coloration. The 'Meibeausai' variety forms white blossoms and the 'Meimonblan' variety forms darker tangerine orange blossoms.

The new variety well meets the needs of the horticultural industry and is particularly well suited for enhancing the appearance of the landscape. It can be grown in a hedge or mass planting.

The new variety has been found to undergo asexual propagation in the South of France and at Wasco, Calif., U.S.A., by a number of routes, including budding, grafting, and cuttage. Asexual propagation by the above-mentioned techniques at these locations has shown that the characteristics of the new variety are stable and are strictly transmissible by such asexual propagation from one generation to another.

The new variety has been named the 'Meipojona', and will be marketed under the TEQUILA GOLD trademark.

BRIEF DESCRIPTION OF THE PHOTOGRAPHS

The accompanying photographs show as nearly true as it is reasonably possible to make the same, in a color illustrations of this character, typical specimens of the new variety. The rose plants of the new variety were two years of age and were observed during June while budded on *Rosa froebelli* understock and growing outdoors near West Grove, Pa., U.S.A.

FIG. 1—illustrates the typical golden yellow blossoms and foliage of the new variety.

Figure 2:
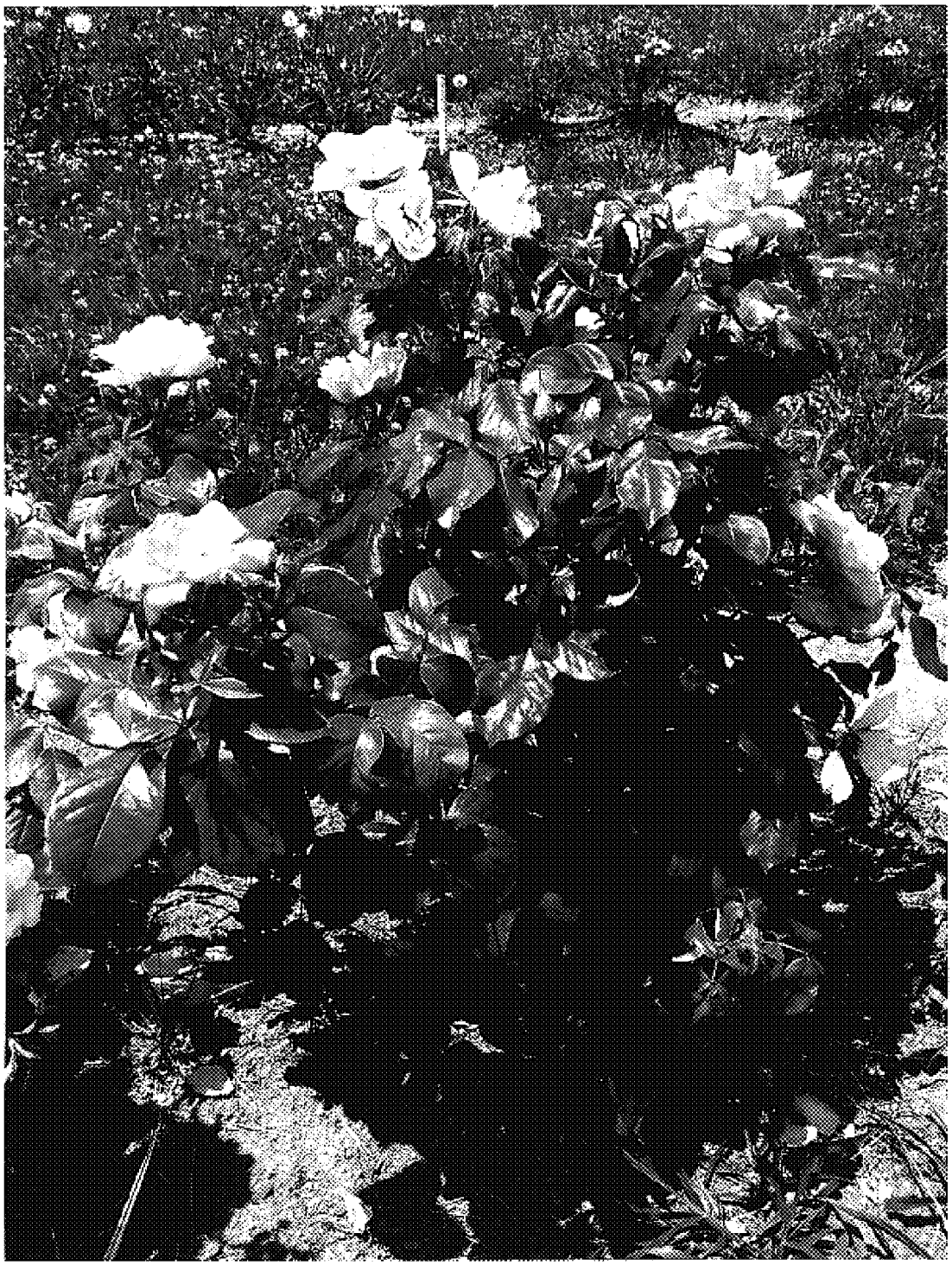

FIG. 2—illustrates a typical flowering plant of the new variety. The vigorous bushy growth habit is shown.

DETAILED DESCRIPTION

The chart used in the identification of the colors is that of The Royal Horticultural Society (R.H.S. Colour Chart). The description is based on the observation of two year-old plants during June while budded on *Rosa froebelli* understock and growing outdoors near West Grove, Pa., U.S.A. Reference to color in common terms is to be accorded its ordinary dictionary significance.

Class: Floribunda.

Plant:

*Height.*—Approximately 80 to 90 cm on average at the end of the growing season.

*Width.*—Approximately 80 to 90 cm on average at the end of the growing season.

*Habit.*—Bushy.

Branches:

*Color.*—Young stems: near Green Group 137A. Adult wood: near Green Group 137B.

*Thorns.*—Configuration: rather upright, longish-pointed on the upper surface and concave on the under surface. On young stems: over a length of 18 cm approximately 5 on average long prickles having lengths over 5 mm that are near Greyed-Purple Group 185D in coloration at the base and near Yellow-Green Group 151D towards the tip. On adult stems: over a length of 19 cm approximately 8 on average long prickles having lengths over 5 mm that are near Greyed-Orange Group 166A in coloration.

Leaves:

*Stipules.*—Adnate, pectinate, approximately 2.5 cm in length, approximately 0.8 cm in width, smooth on the upper surface, tomentose on the under surface, and near Green Group 137C in coloration.

*Petioles.*—Upper surface: rather glandular, and near Green Group 136B in coloration. Under surface: tomentose, and near Green Group 137B and 137C in coloration. Length: approximately 1 to 2 cm on average.

*Rachis.*—Upper surface: rather glandular. Under surface: tomentose.

*Size.*—A five-leaflet leaf including the petiole commonly is approximately 11 cm in length on average and approximately 10.5 cm in width on average.

*Leaflets.*—Number: 3, 5 (most often), and 7. Shape: elliptic with a pointed tip and an obtuse base. Size: terminal leaflets commonly are approximately 7 cm in length on average and approximately 3.5 to 4 cm in width on average. Serration: fine and regular (as illustrated). Texture: smooth, semi-glossy, and of good substance. General appearance: very dense, dark green, and semi-glossy. Color (young foliage): Upper surface: dark green, near Green Group 136A with some anthocyanin coloration of near Greyed-Red Group 178A. Under surface: dark green, near Green Group 137A and suffused with some red anthocyanin coloration. Color (adult foliage): Upper surface: dark green, near Green Group 136A. Under surface: dark green, near Green Group 137A.

Inflorescence:

*Number of flowers.*—Commonly in clusters of 2 to 5 flowers per stem.

*Peduncle.*—Possesses good strength, rigid, very slightly glandular, approximately 2 to 2.5 cm in length on average, and near Green Group 138A in coloration.

*Sepals.*—Upper surface: tomentose and near Yellow-Green Group 148B and 148C in coloration. Under surface: smooth, and near Green Group 137B, 137C, and 137D in coloration. Some small extensions are present. Size: approximately 3 cm in length on average, and approximately 0.9 cm in width at the widest point on average.

*Buds.*—Shape: conical. Size: medium. Length: approximately 1.5 cm on average. Diameter: approximately 1 cm on average. Color upper surface: near Yellow Group 9A and lightly suffused on the first petal whorls with Orange-Red Group 35A as the calyx breaks. Color under surface: near Yellow Group and widely suffused with Orange-Red Group 35A as the calyx breaks. Spot at base: none observed.

*Flower.*—Blooming habit: commonly blooms in clusters from May to November on a substantially continuous basis. Shape: cup-shaped. Diameter: approximately 7 to 9 cm on average when fully open. Color (when blooming): Upper surface: bright golden yellow near Yellow Group 6C. Under surface: near Yellow Group 6D and lightly suffused with Orange-Red Group 35C. Spot at base: none observed. Color stability: some fading with advancing maturity. Petal number: approximately 29 on average under normal growing conditions. Petal arrangement: imbricated. Petal configuration: reflexed tip and an obtuse base. Petal shape: generally oval. Petal size: approximately 3.5 cm in length on average, and approximately 3 cm in width on average. Petal texture: smooth. Petal margin: wavy and somewhat reflexed (as illustrated). Petaloids: very few located at the center, commonly approximately 6 in number on average, generally oval in shape, on the upper surface near Yellow Group 6C and slightly suffused with Orange-Red Group 35A, and on the under surface near Yellow Group 6D and widely suffused with some orange-red coloration. Stamen: approximately 110 on average. Anthers: regularly disposed around the styles, approximately 0.2 cm in size on average, and near Greyed-Orange Group 177A in coloration. Filaments: approximately 0.4 cm in length on average, and near Greyed-Orange Group 165B in coloration. Pistils: approximately 50 on average. Styles: approximately 0.2 cm in length on average, and near Yellow-Green Group 149C in coloration. Stigmas: approximately 0.1 cm in size on average, and near Yellow Group 13B in coloration. Fragrance: none. Lastingness: approximately 15 days on the plant in a garden setting. Petal drop: the petals commonly detach cleanly before drying. Receptacle: smooth, near Green Group 137B suffused with some red anthocyanin coloration, commonly approximately 0.6 to 0.8 cm in length and approximately 0.6 to 0.8 cm in width on average, and in longitudinal section in the shape of a pitcher. Seeds: ovoid in shape, rough in texture, and approximately 0.5 cm in length.

Development:

*Vegetation.*—Very strong.

*Blooming.*—Nearly continuous.

*Tolerance to diseases.*—Very good with respect to Oidium and Black Spot under normal growing conditions.

*Tolerance to heat and cold.*—Good general resistance.

*Aptitude to bear fruit.*—Medium.

I claim:

1. A new and distinct Floribunda rose plant having the following combination of characteristics:

(a) forms on a nearly continuous basis attractive bright golden-yellow blossoms, (b) exhibits a vigorous and bushy growth habit, (c) forms decorative dense dark semi-glossy foliage of good substance, (d) displays good tolerance to Oidium and Black Spot, and (e) is well suited for growing as ornamentation in parks and gardens;

substantially as illustrated and described.

* * * * *